United States Patent [19]

Amschler

[11] Patent Number: 4,665,074
[45] Date of Patent: May 12, 1987

[54] 6-(POLYFLUOROALKOXYPHENYL) PYRIDAZINONES, THEIR COMPOSITIONS, SYNTHESIS AND USE

[75] Inventor: Hermann Amschler, Radolfzell, Fed. Rep. of Germany

[73] Assignee: Byk Gulden Lomberg Chemische Fabrik GmbH, Constance, Fed. Rep. of Germany

[21] Appl. No.: 731,580

[22] Filed: May 7, 1985

[30] Foreign Application Priority Data

May 10, 1984 [CH] Switzerland .................. 2297/84

[51] Int. Cl.$^4$ .................. C07D 237/14; C07D 237/04; C07D 295/14; A61K 31/50
[52] U.S. Cl. .................. 514/247; 544/171; 544/239
[58] Field of Search .................. 544/239; 514/247

[56] References Cited

U.S. PATENT DOCUMENTS 4,397,854 8/1983 Sircar .................. 424/250

FOREIGN PATENT DOCUMENTS 2435244 2/1976 Fed. Rep. of Germany ...... 544/239

OTHER PUBLICATIONS

Baddar et al., *J. Chem. Soc.*, 3342–3348, 1965.
Steck et al., *J. Heterocycl. Chem.*, vol. 11, 755–761, 1974.
Albright et al., *J. Heterocycl. Chem.*, vol. 15, 881–892, 1978.
Schreiber et al., *Bull. Soc. Chim.*, France, 2, 625–629, 1973.
Pitarch et al., *Eur. J. Med. Chem.-Chimica Therapeutica*, vol. 9, No. 6, 644–650, 1974.
Curran et al., *J. Med. Chem.*, vol. 17, No. 3, 273–281, 1974.
Derwent #B03, 18917 1408 for JP8008-015, 1983.
Derwent #B03, 18918 1408 for JP58008016, 1983 Mitsubishi.
Derwent #B02, 16839 C/10 for EP 8391 (Thomae), 3/1980.
Derwent #B03 CO211413x/107 for DT 2435 244 (Lentia), 1974.
Derwent #B03, 33034 C/19 for EP 10156 (Merek), 1980.
Derwent #B03, 67389A/38 for DT2810267 (Sankyo), 9/78.
Derwent #B03, 49295B/27 for DT275923 (Hoechst), 1979.
Derwent B03 CO2 30268x/17 for DT2445681 (Lentia), 1976.

Primary Examiner—Mark L. Berch
Attorney, Agent, or Firm—Berman, Aisenberg & Platt

[57] ABSTRACT 6-aryl-3[2H]pyridazinones of formula I

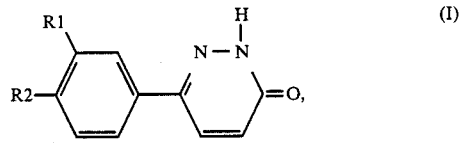

(I)

in which one of the substituents R1 and R2 denotes hydrogen or (C1–C4)-alkoxy, and the other denotes polyfluoro-(C1–C4)-alkoxy, and their pharmacologically-tolerated salts are suitable as bronchospasmolytic and cardiotonic active compounds. Processes for their preparation and appropriate medicaments are indicated.

13 Claims, No Drawings

6-(POLYFLUOROALKOXYPHENYL) PYRIDAZINONES, THEIR COMPOSITIONS, SYNTHESIS AND USE

FIELD OF THE INVENTION

The invention relates to pyridazinones, the preparation and utilization thereof, and to drugs containing pyridazinones.

BACKGROUND

6-Aryl-3[2H]pyridazinones, as starting materials or intermediates for the synthesis of pharmaceuticals and plant protection agents, and a process for their preparation are described, for example, by Baddar et al. (J. Chem. Soc. 1965, 3342), Steck [J. Heterocycl. Chem. 11 (1974) 755], Albright et al. [J. Heterocycl. Chem. 15 (1978) 625], Pitarch et al. [Eur. J. Med. Chem-Chimica Therapeutica 9 (1974) 644] and Curran et al. [J. Med. Chem. 17 (1974) 273] or are known, inter alia, from the following descriptions: German Offenlegungsschrift Nos. 2,435,244, 2,445,681 and 2,757,923.

6-aryl-3[2H]pyridazinones are also known from, for example, the following descriptions: German Offenlegungsschrift Nos. 2,427,943, 2,810,267, 2,845,220, European Offenlegungsschrift Nos. 8,391, 10,156, Japanese Preliminary Published Application No. 58,008,105 and U.S. Pat. No. 4,397,854.

SUMMARY OF THE INVENTION

The invention relates to 6-aryl-3[2H]pyridazinones of formula I

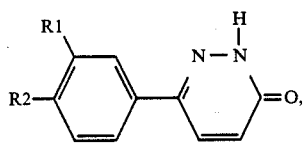

in which one of the substituents R1 and R2 denotes hydrogen or C1–C4-alkoxy, and the other denotes polyfluoro-C1–C4-alkoxy, and to their pharmacologically-tolerated salts with bases. These compounds have advantageous pharmacological properties.

Polyfluoro-C1–C4-alkoxy is straight-chain or branched C1–C4-alkoxy in which at least two hydrogen atoms are replaced by fluorine atoms. A straight-chain C1–C3-alkoxy group in which at least two hydrogen atoms are replaced by fluorine is preferred. Preferred polyfluoroalkoxy groups are difluoromethoxy, trifluoromethoxy, 1,1,2,2-tetrafluoroethoxy and 1,1,1-trifluoroethoxy.

C1–C4-alkoxy is straight-chain or branched. The methoxy group is preferred.

Suitable salts are salts with inorganic bases. The cations used for the salt formation are particularly the cations of the alkali metals or of the alkaline earth metals.

The invention also relates to the use of the compounds of formula I for preparing medicaments for the treatment or prophylaxis of diseases based on disorders of the bronchi and/or cardiac insufficiency, or for strengthening the heart.

The invention furthermore relates to a process for preparing the 6-aryl-3[2H]pyridazinones of formula I and their pharmacologically-tolerated salts with bases, which comprises (a) oxidizing a 6-aryltetrahydropyridazinone of formula II

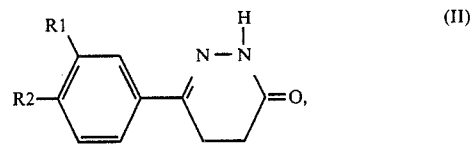

in which R1 and R2 have their previously-ascribed meanings, and, if desired, then converting the resulting pyridazinone into a salt, or (b) reacting a morpholinobutyric acid of formula III

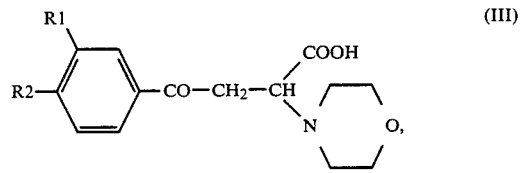

in which R1 and R2 have the same meanings, with hydrazine and, if desired, then converting the resulting pyridazinone into a salt, or (c) reacting an acrylic acid of formula IV

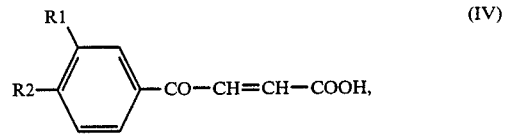

in which R1 and R2 have the indicated meanings, with hydrazine and, if desired, then converting the resulting pyridazinone into a salt.

An object of this invention is to provide new compounds having a bronchospasmolytic action equal to or surpassing that of theophylline.

A further object is to provide new compounds having a cardiotonic action equal to or surpassing that of theophylline.

Another object is to provide compounds and medicinal compositions useful in human and veterinary medicine for the treatment and prophylaxis of diseases involving disorders of the bronchi.

A still further object of the invention is to provide compounds and medicinal compositions useful in human and /veterinary medicine for treating diseases involving cardiac insufficiency and/or for strengthening the heart.

DETAILS

The oxidation (dehydrogenation) according to process variant (a) is carried out by methods which are known to the expert. For example, the dehydrogenation is optionally effected in the presence of a noble metal of the eighth subgroup, for example palladium or platinum (German Offenlegungsschrift No. 2,757,923); using chromium trioxide (Overend et al., J. Chem. Soc. 1947, 239); using nitrobenzenesulfonic acids or nitronaphthalenesulfonic acids, preferably using their sodium or ammonium salts (British Patent Specification 1,168,291).

The reaction according to process variant (b) is carried out by a method analogous to that of Schreiber et al. [Bull. Soc. Chim. France 2 (1973) 625]. For example, the morpholinobutyric acid III, which is formed as an intermediate, is reacted with hydrazine hydrate under reflux in a lower alkanol, for example n-butanol. Alternatively, the morpholinium salt of compound III, obtained by reaction of the appropriate acetophenone with glyoxylic acid and morpholine, is reacted with hydrazine hydrate in acid solution.

The reaction according to process variant (c) is carried out by methods which are known to the expert. For example, compounds IV are reacted, in a manner analogous to that in German Offenlegungsschrift 2,445,681, with methanol or aqueous methanol at room temperature or slightly elevated temperature in the presence of a basic compound, such as an alkali-metal carbonate, hydroxide or lower alkanolate, a tert.-amine or ammoniumhydroxide; the acid is liberated from the resulting salt, and this acid is heated with 1 to 1.6 mols of hydrazine hydrate, at least a neutral medium (preferably an acid medium) being maintained.

The 6-aryl-3[2H]pyridazinones I are converted into salts by methods which are known to the expert. The alkaline reactant which is used is that inorganic or organic base whose salt is desired. The salts are obtained by, for example, reacting the pyridazinones I with the stoichiometric equivalent of the appropriate base, for example sodium hydroxide or sodium methanolate, or by converting readily soluble salts into sparingly soluble salts by double decomposition.

The compounds II, III and IV are known or are prepared by known processes from available starting materials.

The examples which follow serve to illustrate the invention in detail. M.P. denotes melting point, and temperatures are given in °C. the yields are given as a percentage of the theoretically calculated amount (% of theory).

EXAMPLE 1

6-(4-trifluoromethoxyphenyl)-3[2H]pyridazinone (a) 27 g of 4-trifluoromethoxyacetophenone are heated with 13.7 g of glyoxylic acid monohydrate at 110° for 2 hours. The melt is cooled to 50°, dissolved in 100 ml of water and 14 ml of aqueous 25% strength ammonia solution, and 7 ml of hydrazine hydrate are added. The thus-obtained mixture is boiled under reflux for 1 hour. The title compound crystallizes out on cooling. It is filtered off with suction, dried in vacuo and recrystallized from isopropanol. 15.9 g (62.1% of theory) are obtained with an M.P. of 200°.

The following are prepared by the same method: 6-[4-(1,1,2,2-tetrafluoroethoxy)phenyl]-3[2H]pyridazinone, M.P. 178° (80.4% of theory), 6-[3-(1,1,2,2-tetrafluoroethoxy)phenyl]-3[2H]pyridazinone, M.P. 155° (70.7% of theory).

(b) 4-trifluoromethoxyacetophenone 40 g of 4-trifluoromethoxybenzoic acid are boiled under reflux in 120 ml of thionyl chloride for 3 hours. Excess thionyl chloride is removed by distillation under atmospheric pressure, and the thus-produced 4-trifluoromethoxybenzoyl chloride is fractionally distilled in vacuo. 37.9 g (87% of theory) of boiling point 82° at 3.3 kPa are obtained.

A solution of magnesium dimethyl malonate is prepared from 4.1 g of magnesium turnings in 25 ml of absolute ethanol and 19.9 ml of dimethyl malonate and 1 ml of carbon tetrachloride. 37.9 g of 4-trifluoromethoxybenzoyl chloride in 85 ml of absolute ether (diethylether) are added dropwise to this solution (while cooling in ice); the cooling bath is then removed, and the reaction mixture is stirred at 20° overnight. Thereafter, while cooling in ice, 25 ml of 25% strength sulfuric acid are added dropwise, the ether layer is removed, and the aqueous phase is extracted twice more with ether. The combined ether extracts are washed with water to neutrality, dried over sodium sulfate and evaporated. The remaining yellow oil is boiled in 300 ml of 6N hydrochloric acid under reflux for 12 hours. After cooling, the oil is removed, the aqueous phase is extracted 6 times with 100 ml of dichloromethane each time. The oil and the dichloromethane extracts are combined, dried over sodium sulfate and evaporated. The remaining oil is distilled at 1.6 kPa. 26.85 g (77.9% of theory) of the title compound (boiling point 94° to 96°). are obtained.

EXAMPLE 2

6-(4-trifluoromethoxyphenyl)-3[2H]pyridazinone 8.7 g of glyoxylic acid monohydrate are boiled in 50 ml of ethanol until dissolution is complete, then 16.5 g of morpholine and 19.5 g of 4-trifluoromethoxyacetophenone are added, and the mixture is stirred at 50° for 16 hours. The reaction mixture is evaporated in vacuo, and the semisolid residue is dissolved in 50 ml of n-butanol; 7.0 g of hydrazine hydrate are added, and the mixture is boiled under reflux for 8 hours. Then the reaction mixture is evaporated in vacuo, and the residue is boiled in 100 ml of 2N hydrochloric acid, filtered off with suction and washed with water until free of acid. After drying and crystallization from isopropanol, 8.4 g (45.4% of theory) of the title compound (M.P. 200°) are obtained.

EXAMPLE 3

6-[4-(1,1,2,2-tetrafluoroethoxyphenyl)-3[2H]pyridazinone 11.8 g of 4-(1,1,2,2-tetrafluoroethoxy)acetophenone and 4.6 g of glyoxylic acid monohydrate are mixed and heated at 120° for 1.5 hours. The melt is cooled and dissolved in 100 ml of methanol; 7.5 g of potassium carbonate are added, and the mixture is heated at from 50° to 60° for 1 hour. After standing overnight, the mixture is acidified with 9.1 ml of concentrated hydrochloric acid; 2.6 ml of hydrazine hydrate are added, and the mixture is boiled under reflux for 3 hours. Then it is acidified to pH 1 with hydrochloric acid, and 75 ml of methanol are distilled off over the course of 2 hours. The mixture is allowed to cool, and the mass of crystals is filtered off with suction, suspended several times in water, filtered off with suction and finally dried in vacuo. 8.2 g (56.9% of theory) of the title compound (M.P. 178°) are obtained.

EXAMPLE 4

6-(4-difluoromethoxy-3-methoxyphenyl)-3[2H]pyridazinone (a) 15 g of 4-difluoromethoxy-3-methoxyacetophenone are heated with 5.9 g of glyoxylic acid monohydrate at 110° for 2 hours. The melt is then cooled to 60°, 30 ml of water are added, and dissolution is brought about by addition of 10 ml of concentrated aqueous ammonium solution. 3.2 g of hydrazine hydrate are added, and the mixture is boiled under reflux for 2 hours, during which the title compound gradually crystallizes out. After cooling, the precipitate is filtered off with suction, thoroughly washed with water, dried and recrystallized from isopropanol. 10.8 g (58.1% of theory) of the title compound (M.P. 204°) are obtained.

The following are prepared by the same method:
6-(3-difluoromethoxy-4-methoxyphenyl)-3[2H]pyridazinone, M.P. 176° (42.2% of theory),
6-(4-difluoromethoxyphenyl)-3[2H]pyridzinone, M.P. 168° (53.9% of theory),
6-(3-difluoromethoxyphenyl)-3[2H]pyridazinone, M.P. 170° (87.5% of theory).

(b) 4-difluoromethoxy-3-methoxyacetophenone 20.8 g of 4-hydroxy-3-methoxyacetophenone are dissolved in 350 ml of dioxane and 350 ml of water by the addition of 30 g of sodium hydroxide, and the resulting solution is heated to 60°. While stirring continuously, chlorodifluoromethane is passed into the solution until uptake of the gas stops (about 4 hours). The solution is cooled, and the resulting precipitate is filtered off with suction and washed three times with 40 ml of diethyl ether each time. The solution is diluted with water to twice its volume and likewise extracted three times with 100 ml of diethyl ether each time. The combined ether extracts are dried over magnesium sulfate and evaporated in vacuo; the residue is crystallized from petroleum ether (boiling point 50° to 70°). 19 g (70.4% of theory) of 4-difluoromethoxy-3-methoxyacetophenone (M.P. 68°) are obtained.

The following are prepared by the same method:
3-difluoromethoxy-4-methoxyacetophenone, M.P. 74° (77.8% of theory),
4-difluoromethoxyacetophenone, oil (78.4% of theory),
3-difluoromethoxyacetophenone, oil (85.7% of theory).

COMMERCIAL USEFULNESS

The 6-aryl-3[2H]pyridazinones of formula I have valuable properties which render them commercially useful. Surprisingly, they are distinguished by a bronchospasmolytic and/or cardiotonic action which is, in some cases, considerably superior to that of theophylline.

The bronchospasmolytic activity of the 6-aryl-3[2H]pyridazinones makes it possible to use them in human and veterinary medicine, wherein they are useful for the treatment and prophylaxis of diseases based on disorders of the bronchi. For example, chronic obstructive respiratory diseases (bronchitis, bronchial asthma) in humans and animals and of various origins are advantageously treated with these compounds.

The positive inotropic activity of the 6-aryl-3[2H]pyridazinones makes it possible to use them in human or veterinary medicine, where they are useful for treating diseases (e.g., myocardial insufficiency, cardiac insufficiency, geriatric heart, myocardial infarct, cardiovascular insufficiency, stenocardia associated with deficient cardiac output and coronary insufficiency) which are based on cardiac insufficiency, or for strengthening the heart.

Thus the invention further relates to a procedure for treating mammals which suffer from or are afflicted by one of the noted diseases. The procedure comprises administering to such a mammal a therapeutically-effective and pharmacologically-tolerated amount of one or more of the compounds according to the invention.

The invention further relates to medicaments containing one or more of the 6-aryl-3[2H]pyridazinones of formula I or of their pharmacologically-acceptable salts.

The medicaments are prepared by processes which are known per se, the compounds being used as such or, if appropriate, in combination with one or more suitable pharmaceutical vehicles. When the new pharmaceutical formulations contain at least one pharmaceutical vehicle in addition to active compound, the content of active compound in these formulations is from 0.5 to 95, preferably from 15 to 75, percent by weight of the total mixture.

The active compounds or the medicaments are used in any suitable formulation, provided that the establishment and maintenance of sufficient levels of active compound are ensured. This can be achieved by, for example, oral or parenteral administration in suitable doses. The pharmaceutical formulation of the active compound is usually in the form of a unit dose appropriate for the desired administration. A unit dose is, for example, in the form of a tablet, a coated tablet, a capsule, a suppository or a measured volume of a powder, of a granular material, of a solution, of an emulsion or of a suspension. "Unit dose" in the context of the present invention is a physically discrete unit which contains an individual amount of the active constituent in combination with a pharmaceutical vehicle, the content of active compound in the unit dose corresponding to a fraction or a multiple of a therapeutic individual dose. An individual dose preferably contains the amount of active compound which is given in one administration and which usually corresponds to a whole daily dose or a half, one-third or one-quarter of the daily dose. If only a fraction, such as a half or one-quarter, of the unit dose is required for an individual therapeutic administration, the unit dose is advantageously divisible, for example in the form of a tablet with a breaking groove.

When in the form of unit doses and intended, for example, for administration to humans, the pharmaceutical formulations according to the invention contain, e.g., from about 5 to 250 mg, advantageously from 10 to 200 mg and in particular from 20 to 100 mg, of active compound. Parenteral formulations contain, e.g., from about 1 to 50 mg, advantageously from 3 to 10 mg and in particular from 5 to 25 mg, of active compound. In human medicine, the active compound or compounds are generally administered in a daily dose of from 0.1 to 10, preferably from 0.3 to 5 and in particular from 0.5 to 3, mg/kg of body weight, if appropriate in the form of several, preferably 1 to 3, individual administrations to achieve the desired results. An individual administration contains the active compound or compounds in amounts of from 0.1 to 5, preferably from 0.2 to 3 and in particular from 0.4 to 2, mg/kg of body weight. For administration by inhalation, it is advantageous to administer the active compound or compounds in a daily dose of from 0.1 to 10 mg, preferably from 0.5 to 5 mg and in particular from 1 to 3 mg, if appropriate in the form of several, preferably 1 to 3, individual doses.

Formulations for intravenous administration are expedient, in particular, for acute treatment, for example emergency treatment.

The therapeutic administration of the pharmaceutical formulation is effected from 1 to 4 times daily at fixed or varying points in time, for example before each meal and/or in the evening. However, it may be necessary to deviate from the dosages mentioned, and in particular to do so as a function of the nature, body weight and age of the individual to be treated, the nature and severity of the disorder, the type of formulation and of administration of the medicament, and the period or interval within which administration takes place. In some cases it may be sufficient to manage with less than the indicated amount of active compound, while in other cases the noted amount of active compound must be exceeded. In acute cases, a higher dose is administered at the start of the treatment. After the onset of the desired effect, the dose is reduced to a lower level.

The optimum dosage and type of administration of active compound required in each particular case is fairly readily determined by any expert on the basis of his expert knowledge.

The pharmaceutical formulations as a rule consist of the active compounds according to the invention and non-toxic pharmaceutically-tolerated medicament vehicles, which are used as an admixture or diluent in solid, semisolid or liquid form, or as a means of encasing, for example in the form of a capsule, a tablet coating, a sachet or some other container for the therapeutically-active constituent. A vehicle optionally also serves as a promoter of absorption of the medicament by the body, as a formulating auxiliary, as a sweetener, as a flavor correctant, as a colorant or as a preservative.

Examples of optional oral forms include tablets, coated tablets, hard and soft capsules (for example those made of gelatin), dispersible powders, granules, aqueous and oily suspension, emulsion, solutions or syrups.

Tablets contain, e.g., inert diluents, for example calcium carbonate, calcium phosphate, sodium phosphate or lactose; granulating and dispersing agents, for example corn starch or alginates; binders, for example starch, gelatin or gum arabic; and lubricants, for example aluminum stearate or magnesium stearate, talc or silicone oil. They are optionally, further provided with a coating which is or is not suitable for bringing about delayed dissolution and absorption of the medicament in the gastrointestinal tract, and hence, for example, better tolerance; a protracted effect or a retarded effect are thus achieved. Gelatin capsules contain, e.g., the medicament mixed with a solid diluent, for example calcium carbonate or kaolin, or an oily diluent, for example olive oil, peanut oil or paraffin oil.

Aqueous suspensions, which, if appropriate, are prepared at short notice, optionally contain suspending agents, for example sodium carboxymethylcellulose, methylcellulose, hydroxypropylcellulose, sodium alginate, polyvinyl pyrrolidone, gum tragacanth or gum arabic; dispersing agents and wetting agents, for example polyoxyethylene stearate, heptadecaethyleneoxycetanol, polyoxyethylene sorbitol monooleate, polyoxyethylene sorbitan monooleate or lecithin; preservatives, for example methyl or propyl hydroxybenzoate; flavoring agents; and sweeteners, for example sucrose, lactose, sodium cyclamate, dextrose or invert sugar syrup.

Oily suspensions contain, for example, peanut oil, olive oil, sesame oil, coconut oil or paraffin oil, and thickeners, such as beeswax, hard paraffin or cetyl alcohol; and furthermore sweeteners, flavoring agents and antioxidants.

Water-dispersible powders and granules contain the medicaments mixed with, e.g., dispersing agents, wetting agents and suspending agents, for example those previoulsy mentioned, as well as with sweeteners, flavoring agents and colorants.

Emulsions contain, for example, olive oil, peanut oil or paraffin oil, in addition to emulsifying agents, such as gum arabic, gum tragacanth, phosphatides, sorbitan monooleate or polyoxyethylene sorbitan monooleate, and sweeteners and flavoring agents.

For rectal administration of the medicaments, suppositories which are prepared with the aid of binders (which melt at the rectal temperature), for example cacao butter or polyethylene glycol, are used.

For parenteral administration of the medicaments, sterile, injectable aqueous suspensions, isotonic salt solutions or other solutions which, if appropriate, are prepared at short notice and which contain dispersing agents or wetting agents and/or pharmacologically-tolerated diluents, for example propylene glycol or butylene glycol, are used.

Oral administration of the medicaments is preferred.

Administration of the compounds according to the invention by inhalation is also preferred for use as a bronchospasmolytic. These compounds are administered either directly as powders or by atomizing solutions or suspensions containing the compounds according to the invention. In this context, atomizing is effected in the conventional manner, for example by compressed-air atomizers or ultrasound atomizers. Administration from spray cans, especially those with a conventional metering valve (metered aerosols) is particularly advantageous. Metered aerosols make it possible to provide a defined amount of active compound per actuation of the spray. So-called synchronous inhalers, use of which synchronizes administration of the active compound with inhalation, are of particular advantage here. Suitable synchronous inhalation devices are disclosed, for example, in German Patent Specification Nos. 1,945,257, 1,917,911 and German Offenlegungsschrift No. 2,055,734.

For inhalation purposes, the active compounds are preferably used in micronized form, particle sizes of less than 10 $\mu$m being advantageous. For administration from spray cans, the active compounds are dispersed in customary propellants, preferably with the aid of a dispersing agent. Possible propellants are, for example, mixtures of trichlorofluoromethane (Frigen ® 12), it being possible for all or some of the trichlorofluoromethane to be replaced by 1,1,2-trichlorotrifluoroethane (Frigen ® 113). Possible dispersing agents are, in particular, the soributan esters customary for these purposes (Spane ® from Atlas GmbH) and lecithin. The dispersing agent is dissolved in the propellant component of lower volatility, which has been initially introduced in cooled form. The micronized active compound is stirred, or the micronized active compounds are stirred, into the solution. The dispersion is filled into spray cans. After crimping, the more volatile propellant component is forced in.

The active compound or compound are, alternatively, formulated in micro-encapsulated form, if appropriate together with one or more of the vehicles or additives mentioned.

Tablets containing 100 mg of
6-(4-difluoromethoxy-3-methoxyphenyl)-
3[2H]pyridazinone 40 kg of active compound, 24 kg of lactose and 16 kg of corn starch are granulated with 4 kg of polyvinyl pyrrolidone (molecular weight 25,000) in 5.5 liters of water, and the granules are forced through a sieve of 1.25 mm mesh. After drying, 10 kg of carboxymethyl cellulose, 4 kg of talc and 2 kg of magnesium stearate are added. The granules are compressed on a cam-type machine to form tablets of diameter 9 mm, weight 250 mg and hardness 4 to 5 kg.

Capsules containing 15 mg of
6-(3-difluoromethoxyphenyl)-3[2H]pyridazinone 150 mg of active compound, 845 mg of microcrystalline cellulose and 5 mg of amorphous silica are finely powdered, the powder is mixed thoroughly, and size 4 hard gelatin capsules are filled with the mixture.

Metered aerosol formulation containing
6-[3-(1,1,2,2-tetrafluoroethoxyphenyl)]-3[2H]pyridazinone 0.540 g of Span ® 85 and 0.135 g of aroma are dissolved in 10.215 g of cooled Frigen ® 11. 0.270 g of micronized active compound is stirred into the solution, and 24 ml cans are filled with the mixture. After crimping, 14.971 g of Frigen ® 12 are forced in. With a chamber volume of the metering valve of 126 μl, 1.6 mg of active compound are released as an aerosol per valve stroke.

BIOLOGICAL INVESTIGATIONS

The 6-aryl-3[2H]pyridazinones of formula I have a bronchospasmolytic action which, in at least some cases, is considerably superior to that of theophylline. In addition, compared with theophylline, their action is more organ-selective, as is evident from comparison of the bronchospasmolysis on the isolated, spontaneously contracted chain of tracheal rings of the guinea pig with the positive inotropic action on the electrically-stimulated left atrium of the rat. Theophylline has been used for a long time as a bronchospasmolytic for the treatment of bronchial asthma and other spastic states of the smooth muscle of the bronchi. Its side effects, especially those on the heart and circulation, are known [cf. Ehrhart/Ruschig, Arzneimittel (Medicaments), Verlag Chemie Weinheim/Bergstrasse 1972, Vol. 1, page 341, Vol. 2, page 258; Schulze-Wernighaus Pharmakotherapie 4 (1981) 168 to 177].

In the Tables which follow, the compounds are identified by a serial number:
1: 6-(4-trifluoromethoxyphenyl)-3[2H]pyridazinone
2: 6-[3-(1,1,2,2-tetrafluoroethoxy)phenyl]-3[2H]pyridazinone
3: 6-[4-(1,1,2,2-tetrafluoroethoxy)phenyl]-3[2H]pyridazinone
4: 6-(3-difluoromethoxy-4-methoxyphenyl)-3[2H]pyridazinone
5: 6-(4-difluoromethoxy-3-methoxyphenyl)-3[2H]pyridazinone
6: 6-(4-difluoromethoxyphenyl)-3[2H]pyridazinone
7: 6-(3-difluoromethoxyphenyl)-3[2H]pyridazinone To test the bronchospasmolytic action of the compounds in vitro on a chain of tracheal rings of the guinea pig, such tracheal rings are subjected to the following procedure:

Four parallel chains of tracheal rings (each consisting of 6 individual rings) of guinea pigs (♂ and ♀, 430–600 g) in an organ bath [5 ml, Krebs-Henseleit solution with added phentolamine ($10^{-5}$ mol/l), 37°, initial tension of the organs 2 g, gassing with carbogen] develop a stable, spontaneous tonic contraction after about 20 to 30 minutes. Relaxation of these permanently contracted organs is, e.g., caused (under isometric measurement conditions) by administration of the test substance in concentrations which increase semilogarithmically and cumulatively (for example $1 \times 10^{-6} + 2 \times 10^{-6} + 7 \times 10^{-6} + 2 \times 10^{-5}$ etc. mol/l), a constant relaxation response being waited for after each individual dose of the test substance before the next higher concentration is administered. Over a period of from 20 to 30 minutes, a complete dose/action curve of the test substance is thus obtained. The particular relaxation is expressed as a percentage fraction of the maximum relaxation achieved by administration of (−)isoprenaline ($10^{-6}$ mol/l). The concentration of the test substance which brings about 50% of the maximum relaxation thus achieved, expressed by the negative logarithm of the $EC_{50}$ mol/l: $-1$ g($EC_{50}$), is a measure of the bronchodilator activity.

Testing the positive inotropic action of the compounds in vitro on the electrically-stimulated left atrium of the rat is effected as follows:

Isometric contractions (HSE force sensor K-30; Watanabe recorder, Linear Corder Mark 5) of isolated left atria of rats (♂, 250–300 g) in an organ bath (10 ml, Tyrode nutrient solution, 31°, gassing with carbogen, initial tension of the organs 0.25 g) with electric stimulation (HSE stimulator, 7 V, 3 ms, 2 Hz) are recorded. After an equilibration period of 30 minutes, a dose-dependent increase in the contraction force is brought about by administration of the test substance in concentrations which increase semilogarithmically and cumulatively (for example $1 \times 10^{-6} + 2 \times 10^{-6} + 7 \times 10^{-6} + 2 \times 10^{-5}$ etc. mol/l), a constant inotropic response being waited for after each individual dose of the test substance before the next higher concentration is administered. The particular increase in the contraction force is expressed as a % of the initial value before administration of the substance. The concentration of the test substance which potentiates the contraction force of the atrium by 40% compared with the initial value ($EC_{40pot}$.mol/l), expressed by the negative logarithm of ($EC_{40pot}$.mol/l): $-1$ g($EC_{40pot}$.), serves as a measure of the cardiotonic activity.

The measure used for the organ-selective activity is the ratio between ($EC_{40pot}$.) left atrium and ($EC_{50}$)$_{trachea}$. As a measure of the activity, the ratios between ($EC_{50}$)$_{trachea}$ values and ($EC_{40pot}$.)$_{left\ atrium}$ values of theophylline and the tested compound are given.

The resulting values are listed in Table 1.

TABLE 1

| Serial No. | Bronchospasmolytic and Positive Inotropic Action | | | | |
|---|---|---|---|---|---|
| | A | B | C | D | E |
| 1 | 4.60 | 4.0 | 4.0 | 5.4 | 4.2 |
| 2 | 5.11 | 4.66 | 2.8 | 17.4 | 19 |
| 3 | 5.04 | 4.21 | 6.8 | 13.2 | 6.8 |
| 4 | 5.80 | 5.76 | 1.1 | 85 | 240 |
| 5 | 5.91 | 6.06 | 0.7 | 110 | 469 |
| 6 | 4.92 | 4.49 | 2.7 | 11.2 | 12.9 |
| 7 | 4.84 | <4.0 | >6.9 | 9.3 | — |
| Theophylline | 3.87 | 3.38 | 3.1 | 1 | 1 |

Column A -lg($EC_{50}$)$_{trachea}$
Column B -lg($EC_{40pot}$.)$_{left\ atrium}$
Column C ($EC_{40pot}$.)$_{left\ atrium}$/($EC_{50}$)$_{trachea}$
Column D ($EC_{50}$)$_{theophylline}$/($EC_{50}$)$_{substances}$
Column E ($EC_{40pot}$.)$_{theophylline}$/($EC_{40pot}$.)$_{substance}$ The protective action against acetylcholine-induced bronchospasm is determined on conscious guinea pigs by a method derived from that of T. Olsson, Acta Allergologica 26, 438–447 (1971), as follows:

Guinea pigs (250–350 g) in a closed Plexiglas cylinder (volume: 5 l) are exposed to a mist of acetylcholine (0.06% in 0.9% sodium chloride solution; Heyer Use 77 ultrasonic atomizer) twice at an interval of 20 minutes. The time from the start of atomization until there is onset of a marked struggle to breathe (in certain circumstances, a hypoxic convulsion in the lateral position) is measured and designated the latency perid. The latency period in a control experiment (without administration of substance) is 2 minutes. The test substance is administered orally by gavage (standard dose 100 μmol/kg, volume 1 ml of 4% strength methocel suspension in 0.9% strength sodium chloride solution/kg). After 30 minutes, the animals are again exposed to the mist of acetylcholine, and the latency periods are measured. A prolongation of the latency period to at least double is regarded as a protective action.

The values are listed in Table 2.

TABLE 2

Protective Action against Acetylcholine-Induced Bronchospasm in Conscious Guinea Pigs

| Serial No. | dose (μmol/kg)p.o.* | Test 30 min. p.a. [pvst application] Tripling of the latency period in N of 10 animals |
|---|---|---|
| 2 | 100 | 8 |
| 4 | 100 | 7 |
| 5 | 100 | 9 |
| 6 | 100 | 8 |
| 7 | 100 | 9 |
| Theophylline | 100 | 3 |

*administered in 4% Methocel suspension

It is evident from Table 2 that the protective action against the bronchospasm, induced by acetylcholine atomization in conscious guinea pigs, brought about by the compounds investigated is greater than that of the comparison substance, theophylline.

The invention and its advantages are readily understood from the proceding description. Various changes may be made in the processes of making and using, in the structure of the compounds and in the formulation of the pharmaceutical compositions without departing from the spirit or scope of the invention or sacrificing its material advantages. The synthesis, compounds, compositions and methods of use hereinbefore described are merely illustrative of preferred embodiments.

What is claimed is:

1. A compound of formula I

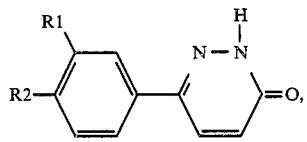

(I)

in which one of R1 and R2 denotes hyrogen or (C1-C4)-alkoxy, and the other denotes polyfluoro-(C1-C4)-alkoxy; or a pharmacologically-acceptable salt thereof with a base.

2. A compound as claimed in claim 1 wherein one of R1 and R2 denotes hydrogen or straight-chain (C1-C3)-alkoxy, and the other denotes polyfluoro-(C1-C2)-alkoxy, or a pharmacologically-acceptable salt thereof with a base.

3. A compound as claimed in claim 1, wherein one of R1 and R2 denotes hydrogen or methoxy, and the other denotes difluoromethoxy, 1,1,2,2-tetrafluoroethoxy or 1,1,1-trifluoroethoxy.

4. The compound of claim 1 which is 6-(4-trifluoromethoxyphenyl)-3[2H]pyridazinone or a pharmacologically-acceptable salt thereof.

5. The compound of claim 1 which is 6[3-(1,1,2,2-tetrafluoroethoxy)phenyl]-3[2H]pyridazinone or a pharmacologically-acceptable salt thereof.

6. The compound of claim 1 which is 6[4-(1,1,2,2-tetrafluoroethoxy)phenyl]-3[2H]pyridazinone or a pharmacologically-acceptable salt thereof.

7. The compound of claim 1 which is 6-(4-difluoromethoxy-3-methoxyphenyl)-3[2H]pyridazinone or a pharmacologically-acceptable salt thereof.

8. A compound as claimed in claim 1, wherein one of R1 and R2 denotes hydrogen or methoxy, and the other denotes trifluoromethoxy.

9. A medicament composition containing a pharmaceutically-acceptable vehicle and at least one member selected from the group consisting of a compound as claimed in claim 1 and a pharmacologically-acceptable salt thereof, the composition comprising from 0.5 to 95 percent by weight of the member.

10. A medicament composition of claim 9 wherein the member is in:

(a) an aqueous suspending-agent-containing suspension,
(b) an oily suspension,
(c) water-dispersible powder,
(d) water-dispersible granules,
(e) an emulsion,
(f) a suppository,
(g) a sterile, injectable aqueous suspension,
(h) an isotonic salt solution,
(i) micronized form,
(j) a tablet,
(k) a capsule,
(l) a sachet, or
(m) a syrup.

11. A method which comprises administering to a subject, prone to or afflicted with a disorder of the bronchi and/or cardiac insufficiency, an effective amount of a compound of formula I of claim 1 or a salt thereof for prophylaxis or treatment of the disorder and/or insufficiency.

12. A method which comprises administering to a subject in need of such treatment a heart-strengthening amount of a compound of claim 1 or of a salt thereof.

13. A medicament composition as claimed in claim 9 having an effective amount, per dosage unit, of the member for treating disorders of the bronchi.

* * * * *